(12) United States Patent
Gupta et al.

(10) Patent No.: US 7,743,766 B2
(45) Date of Patent: *Jun. 29, 2010

(54) AEROSOL GENERATING DEVICES AND METHODS FOR GENERATING AEROSOLS HAVING CONTROLLED PARTICLE SIZES

(75) Inventors: Rajiv Gupta, Glen Allen, VA (US); Douglas D. McRae, Chesterfield, VA (US); Kenneth A. Cox, Powhatan, VA (US); Walter A. Nichols, Chesterfield, VA (US)

(73) Assignee: Philip Morris USA Inc., Richmond, VA (US)

(*) Notice: Subject to any disclaimer, the term of this patent is extended or adjusted under 35 U.S.C. 154(b) by 634 days.

This patent is subject to a terminal disclaimer.

(21) Appl. No.: 11/140,984

(22) Filed: Jun. 1, 2005

(65) Prior Publication Data

US 2005/0205084 A1  Sep. 22, 2005

Related U.S. Application Data

(63) Continuation of application No. 10/654,980, filed on Sep. 5, 2003, now Pat. No. 6,923,179.

(60) Provisional application No. 60/408,291, filed on Sep. 6, 2002.

(51) Int. Cl.
*F24F 3/14* (2006.01)
*F23D 11/00* (2006.01)
*H05B 3/00* (2006.01)
*A61M 15/00* (2006.01)

(52) U.S. Cl. .................. 128/203.26; 128/203.27; 128/203.12; 128/200.24; 261/104

(58) Field of Classification Search ............ 128/200.14, 128/203.12, 203.15, 200.12, 203.17, 203.26, 128/203.27, 203.28, 200.23; 261/130, 154, 261/177, 104, DIG. 65; 239/13, 74, 43, 44, 239/67–71, 128, 135, 136, 338; 422/303, 422/125; 392/303, 386, 392
See application file for complete search history.

(56) References Cited

U.S. PATENT DOCUMENTS 4,046,146 A    9/1977   Rosskamp et al.
4,251,032 A *  2/1981   Werding ................ 239/323

(Continued)

FOREIGN PATENT DOCUMENTS

WO           01/21319 A1    3/2001

(Continued)

OTHER PUBLICATIONS

Notification of Transmittal of the International Search Report or the Declaration dated Dec. 24, 2003 for PCT/US03/27730.

(Continued)

*Primary Examiner*—Justine R Yu
*Assistant Examiner*—Annette F Dixon
(74) *Attorney, Agent, or Firm*—Buchanan Ingersoll & Rooney PC

(57) ABSTRACT

An aerosol generating device includes a housing, a heater and an optional mouthpiece. The heater volatilizes liquid within a flow passage and forms an aerosol in the mouthpiece. An aerosol confinement sleeve is disposed to control the size distribution of the aerosol.

18 Claims, 14 Drawing Sheets

U.S. PATENT DOCUMENTS

| | | | |
|---|---|---|---|
| 4,260,110 A * | 4/1981 | Werding | 239/404 |
| 4,627,432 A | 12/1986 | Newell et al. | |
| 4,811,731 A | 3/1989 | Newell et al. | |
| 4,935,624 A | 6/1990 | Henion et al. | |
| 5,381,957 A * | 1/1995 | Bianco | 239/99 |
| 5,474,059 A * | 12/1995 | Cooper | 128/200.22 |
| 5,522,385 A | 6/1996 | Lloyd et al. | |
| 5,743,251 A | 4/1998 | Howell et al. | |
| 5,865,185 A * | 2/1999 | Collins et al. | 131/194 |
| 5,881,714 A * | 3/1999 | Yokoi et al. | 128/200.14 |
| 5,894,841 A | 4/1999 | Voges | |
| 5,954,047 A | 9/1999 | Armer et al. | |
| 5,957,124 A | 9/1999 | Lloyd et al. | |
| 5,964,223 A | 10/1999 | Baran | |
| 6,012,647 A | 1/2000 | Ruta et al. | |
| 6,116,516 A | 9/2000 | Gañán-Calvo | |
| 6,153,173 A | 11/2000 | Sapsford et al. | |
| 6,155,268 A * | 12/2000 | Takeuchi | 131/273 |
| 6,158,676 A * | 12/2000 | Hughes | 239/405 |
| 6,234,167 B1 | 5/2001 | Cox et al. | |
| 6,267,297 B1 * | 7/2001 | Contadini et al. | 239/1 |
| 6,293,279 B1 * | 9/2001 | Schmidt et al. | 128/200.23 |
| 6,443,146 B1 * | 9/2002 | Voges | 128/200.14 |
| 6,528,018 B1 | 3/2003 | Berndt | |
| 6,568,390 B2 | 5/2003 | Nichols et al. | |
| 6,701,922 B2 | 3/2004 | Hindle et al. | |
| 6,759,029 B2 * | 7/2004 | Hale et al. | 424/45 |
| 6,883,516 B2 * | 4/2005 | Hindle et al. | 128/200.14 |
| 6,923,179 B2 * | 8/2005 | Gupta et al. | 128/203.17 |
| 2002/0079309 A1 | 6/2002 | Cox et al. | |
| 2002/0079377 A1 | 6/2002 | Nichols | |
| 2004/0016427 A1 | 1/2004 | Byron et al. | |
| 2004/0060999 A1 * | 4/2004 | Kock | 239/136 |
| 2004/0079368 A1 * | 4/2004 | Gupta et al. | 128/203.12 |
| 2005/0235991 A1 * | 10/2005 | Nichols et al. | 128/204.17 |

FOREIGN PATENT DOCUMENTS

WO      01/81182 A2    11/2001

OTHER PUBLICATIONS

Notification of Transmittal of International Preliminary Examination Report dated Jun. 28, 2004 for PCT/US03/27730.
Supplementary European Search Report dated Jun. 20, 2008 for EP 03752007.9.

* cited by examiner

AEROSOL GENERATING DEVICES AND METHODS FOR GENERATING AEROSOLS HAVING CONTROLLED PARTICLE SIZES

This application is a continuation application of U.S. application Ser. No. 10/654,980 entitled AEROSOL GENERATING DEVICES AND METHODS FOR GENERATING AEROSOLS HAVING CONTROLLED PARTICLE SIZES, filed on Sep. 5, 2003 now U.S. Pat. No. 6,923,179, the entire content of which is hereby incorporated by reference.

RELATED APPLICATIONS

This application claims priority under 35 U.S.C. §119 to U.S. Provisional Application No. 60/408,291 entitled AEROSOL GENERATING DEVICES AND METHODS FOR GENERATING AEROSOLS HAVING CONTROLLED PARTICLE SIZES and filed on Sep. 6, 2002, the entire content of which is hereby incorporated by reference.

BACKGROUND

Aerosols are useful in a wide variety of applications. For example, aerosols have been used to treat respiratory ailments, or to deliver medicaments, by providing sprays of finely divided particles of liquids and/or solids, such as powders, liquid medicaments, and the like, which are inhaled by patients. Aerosols are also useful, for example, for delivering desired scents to rooms, applying scents to the skin, and delivering paints and lubricants.

There are various known techniques for generating aerosols. For example, U.S. Pat. Nos. 4,811,731 and 4,627,432 disclose devices for administrating medicaments to patients that include a capsule, which is pierced to release medicament in powder form. The user inhales the released medicament through an opening in the device. Medicaments in liquid form have been delivered by generating aerosols with a manually operated pump. The pump draws liquid from a reservoir and forces it through a small opening to form a fine spray.

Alternatively, medicaments have been delivered by generating an aerosol including liquid or powder particles using a compressed propellant, which entrains the medicament. Such inhalers are usually operated by depressing an actuator to release a charge of the compressed propellant, which contains the medicament, through a spray nozzle, allowing the propellant encapsulated medicament to be inhaled by the user. However, it is difficult to properly synchronize the inhalation of the medicament with depression of the actuator. Further, desired quantities of medicament or other materials are not suitably delivered by this method.

Many aerosol generating devices also are unable to generate aerosols having an average mass median aerosol diameter (MMAD) less than 2 to 4 microns, and to deliver high aerosol mass flow rates, such as above 1 milligram per second, with particles in the size range of 0.2 to 2.0 microns. A high aerosol mass flow rate and small particle size are particularly desirable for enhanced penetration into the lungs during medicament administration, such as for asthma treatment.

Larger particles generated by inhalers may be deposited in the mouth and pharynx of the patient, rather than inhaled into the lungs. In addition, larger inhaled particles may not penetrate into the lungs as deeply as desired for certain applications.

Therefore, there is a need for an aerosol generating device that can provide different aerosol size distributions of aerosols, such that the device can be adapted to the different needs of a patient. Moreover, there is a need for an aerosol generating device that provides controlled adjustability of the aerosol size distribution of aerosols that it produces.

SUMMARY

An aerosol generating device is provided that can produce aerosols having different aerosol size distributions. The aerosol generating device provides controlled adjustability of the aerosol size distribution, such that it can be used to provide aerosols that are most suitable to meet the needs of a user.

In a preferred embodiment, the aerosol generating device comprises a housing, a flow passage, a heater, a mouthpiece, a source of liquid to be volatilized, and an aerosol confinement sleeve. Liquid is supplied into the flow passage from the source and heated in the flow passage by the heater, thereby volatilizing the liquid. The aerosol confinement sleeve is disposed about the outlet end of the flow passage. Volatilized material exiting the flow passage enters into the aerosol confinement sleeve, which is configured to control the aerosol size distribution delivered by the aerosol generating device.

An embodiment of a method for generating an aerosol comprises supplying a liquid to a flow passage; heating the liquid in the flow passage to volatilize the liquid; and passing volatilized liquid out of the flow passage and into an aerosol confinement sleeve configured to control an aerosol size distribution of an aerosol produced from the volatilized liquid.

DRAWINGS

DETAILED DESCRIPTION

An aerosol generating device is provided, which can be operated to produce aerosols having a controlled particle size distribution. The aerosol generating device includes an aerosol confinement sleeve, which controls the particle size distribution of aerosols. In a preferred embodiment, the aerosol generating device includes a replaceable aerosol confinement sleeve, which permits a user or manufacturer to change the aerosol confinement sleeve to provide a different aerosol particle size distribution.

Figure 1:
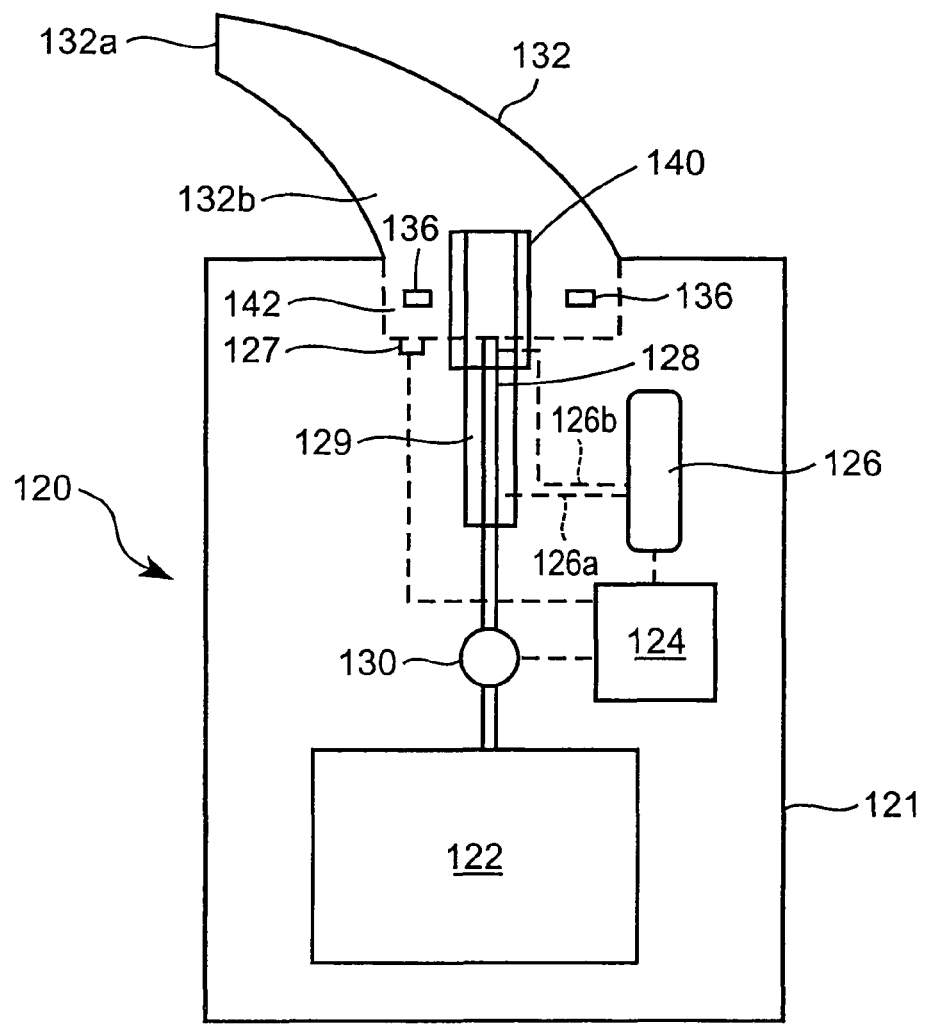
FIG. 1 illustrates an embodiment of an aerosol generating device.

FIG. 1 depicts a preferred embodiment of a hand-held aerosol generating device 120. The aerosol generating device 120 comprises a housing 121, a source 122 of a liquid aerosol formulation, a controller 124, a power source 126, an optional sensor 127, such as a pressure sensor, a heated flow passage 128, a valve 130, and a mouthpiece 132. The valve 130 is operable to deliver a volume of fluid, such as a predetermined dose, from the source 122 to the flow passage 128.

The controller 124 is operably connected to the power source 126, the sensor 127 and valve 130 to effect delivery of the liquid from the source 122 to the flow passage 128, and to operate a heater arranged to heat liquid in the flow passage 128. For example, in a preferred embodiment, the flow passage comprises a capillary sized flow passage. For example, the capillary sized flow passage can be tube or alternatively a passage in a body, such as a monolithic or multilayer body of an electrically insulating material.

In a preferred embodiment, the heated flow passage 128 comprises an electrically conductive material, such as a metallic tube (e.g., stainless steel), or a non-conductive or semi-conductive tube incorporating a heater made of an electrically conductive material, such as platinum, or the like. The flow passage is preferably a capillary sized passage of uniform cross-section along its length. In such embodiments, the flow passage can have any suitable diameter, preferably between about 0.1 to 10 mm, more preferably about 0.1 to 1 mm, and most preferably about 0.15 to 0.5 mm. However, in other embodiments, the capillary passage can have other non-uniform cross-sectional configurations, which are defined by a maximum transverse dimension or width, or by a transverse cross-sectional area. For example, in a preferred embodiment, the capillary passage can have a transverse cross-sectional area from about $8 \times 10^{-5}$ mm$^2$ to about 80 mm$^2$, preferably about $2 \times 10^{-3}$ mm$^2$ to about $8 \times 10^{-1}$ mm$^2$, and more preferably about $8 \times 10^{-3}$ mm$^2$ to about $2 \times 10^{-1}$ mm$^2$.

Figure 2:
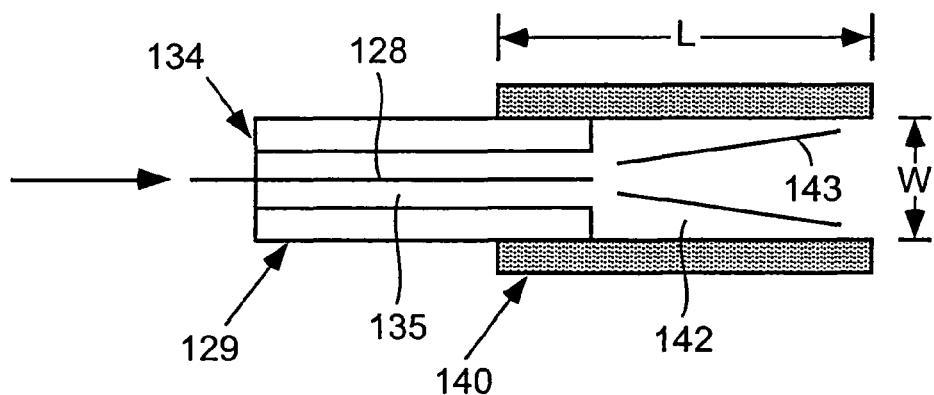
FIG. 2 illustrates an embodiment of an arrangement including an aerosol confinement sleeve located at the outlet end of a flow passage.

The flow passage 128 may be configured to extend in a linear or non-linear direction. As shown in FIGS. 1 and 2, a portion of the flow passage 128 is disposed within a body 129. In a preferred embodiment, the flow passage 128 comprises a section of tubing supported coaxially within the body 129. The body 129 has an inner transverse dimension or width larger than the tubing forming the flow passage. In a preferred embodiment, a rear wall 134 of the body 129 forms a seal about the outer surface of the tube defining the flow passage 128 to form a dead air space 135 between the tube defining the flow passage 128 and the body 129. The body 129 is preferably air impermeable.

The body 129 can have various shapes, such as cylindrical, oval, polygonal, or conical. The body can be any suitable material, such as a metal, ceramic, polymer, glass, or a mixture or composite thereof. In a preferred embodiment, the body is made of a thermally insulating material to minimize loss of heat of air within the space 135 and thereby minimize heat loss from the tube defining the flow passage 128. By minimizing heat loss from the flow passage, it is possible to reduce the time needed to heat the flow passage to a desired temperature to vaporize liquid in the flow passage, and/or to heat the flow passage to a more uniform temperature. In a preferred embodiment, the flow passage can be heated by passing electrical current through a heater comprising a resistive heating material, such as a section of metal tubing forming the flow passage, or a separate heater can be located along the flow passage. For example, direct current can be passed through resistive heating material via electrical lines 126a, 126b attached to positive and negative electrodes of battery 126.

As shown in FIG. 2, an aerosol confinement sleeve 140 is provided about the body 129 and flow passage 128. As described in detail below, the aerosol confinement sleeve 140 controls the aerosol particle size of aerosols delivered by the aerosol generating device 120.

In the aerosol generating device 120 shown in FIG. 1, when the controller 124 activates the power supply to pass electrical current through the heater formed by the resistive heating material, liquid in the flow passage 128 is heated to a sufficient temperature to be vaporized. In a preferred embodiment, the aerosol generating device 120 includes a power supply, which supplies electric current to the heater formed by a portion of a metallic tube, such as a stainless steel tube, between electrical contacts (not shown) on the tube to which lines 126a and 126b are attached. However, in embodiments where the aerosol generating device is a larger laboratory or industrial unit, power can be supplied by an external power source. As the power supply supplies electric current, the electric current resistively heats the heater material, thereby causing volatilization of liquid within the flow passage 128. In a preferred embodiment, the controller 124 is programmed to activate the power supply in an intermittent manner so as to heat the flow passage 128 for a predetermined time interval during which a predetermined volume of fluid is supplied to the flow passage 128 from the source 122.

In other preferred embodiments, other arrangements can be used to volatilize liquid within the flow passage 128. For example, a preferred embodiment comprises a laminate body including opposed layers bonded together, and a flow passage disposed between the layers, as described in commonly-assigned U.S. application Ser. No. 09/742,320 filed Dec. 22, 2000, the disclosure of which is hereby incorporated by reference in its entirety.

In another preferred embodiment, an inductive heating arrangement can be used, such as the arrangement disclosed in commonly-assigned U.S. application Ser. No. 09/742,323 filed on Dec. 22, 2000, the disclosure of which is hereby incorporated by reference in its entirety. In a preferred embodiment, a current is passed through one or more inductive heating coils to produce an electromagnetic flux in an electrically conductive heating element, which is located such that the flux produces eddy currents inside the heating element, which in turn heats the heating element. This heat is then transferred to the liquid within the flow passage 128 either by direct or indirect thermal conduction.

In another preferred embodiment, the heating arrangement includes a resistance heater, such as a thin platinum layer, located along the flow passage, as described in commonly-assigned U.S. Pat. Nos. 5,743,251 and 6,234,167, each of which is hereby incorporated by reference in its entirety.

In a preferred embodiment, the mouthpiece 132 has a volumetric capacity of from about 5 $cm^3$ to about 10 $cm^3$. The mouthpiece 132 includes a mouthpiece opening 132a through which aerosol generated by the aerosol generating device 120 exits to a patient inhaling the aerosol. In order to supply air for mixing with the volatilized liquid exiting from the flow passage 128, the aerosol generating device 120 can include one or more air passages 136 to permit the passage of external air into the aerosol generating device 120. The external air passes into the interior space 132b defined by the mouthpiece 132. The external air inside the mouthpiece 132 admixes with the volatilized liquid exiting the heated flow passage 128 within the mouthpiece 132. The mouthpiece opening 132a is separated from the outlet-end of the heated flow passage 128 so that air passing into the space 132b admixes with the volatilized liquid prior to exiting through the mouthpiece opening 132a. Other gases (e.g., inert gases, nitrogen, or the like) suitable for dilution of medicament within the aerosol generating device may be mixed with the volatilized fluid exiting the heated flow passage 128.

During operation of the aerosol generating device 120, the valve 130 may be opened to allow a desired volume of liquid material from the source 122 to enter the flow passage 128. The valve 130 may be opened either prior to or subsequent to detection by the sensor 127 of vacuum pressure applied to the mouthpiece 132 by a user attempting to inhale aerosol from the aerosol generating device 120. Liquid passing through the flow passage 128 is heated to a sufficient temperature to volatilize the liquid. Liquid from the source 122 can be fed into the flow passage 128 at a substantially constant pressure and/or in a predetermined volume. The volatilized liquid exits the flow passage 128 through an outlet end of the flow passage 128 and forms an aerosol, which can be inhaled by a user drawing upon the mouthpiece 132.

The aerosol confinement sleeve 140 is provided in the aerosol generating device 120 to control the size distribution of aerosol particles that are generated by the aerosol generating device 120. As shown in FIG. 2, in a preferred embodiment, the aerosol confinement sleeve 140 is disposed at the outlet end of the flow passage 128 and body 129 surrounding the flow passage. The aerosol confinement sleeve 140 has a length, L, a largest cross-sectional dimension, W, and an interior space 142 having an interior volume. In a preferred embodiment, the length L of the aerosol confinement sleeve 140 is from about ¼ inch to about 4 inches; dimension W is from about ¼ inch to about 2 inches; the ratio of the dimension W to the length L is from about 1:1 to about 0.25:4; and the interior volume of the aerosol confinement sleeve 140 is from about 0.05 $in^3$ to about 50 $in^3$. In another preferred embodiment, the length L of the aerosol confinement sleeve 140 is from about ⅛ inch to about 2 inches, and dimension W is from about ⅛ inch to about ½ inch.

The shape of the aerosol confinement sleeve 140 is not limited. The aerosol confinement sleeve 140 can have any suitable shape, such as cylindrical, oval, polygonal, or conical. In a preferred embodiment, the aerosol confinement sleeve 140 is tubular and sized to fit closely onto the body 129. The aerosol confinement sleeve 140 can be made of any suitable material, such as a metal, ceramic, polymer, glass, or a mixture thereof. In a preferred embodiment, the aerosol confinement sleeve is air impermeable.

The length L and dimension W of the aerosol confinement sleeve 140 can be varied to control the size distribution of aerosol particles delivered by the aerosol generating device 120. As described below, it has been determined that for a given flow rate of liquid in the flow passage 128, increasing the length L of the aerosol confinement sleeve 140 having a given dimension W can increase the mass median aerodynamic diameter (MMAD) of aerosol particles delivered by the aerosol generating device. Thus, by controlling the dimension W and length L of the aerosol confinement sleeve 140, a selected aerosol size distribution or mass median aerodynamic diameter of aerosol particles can be delivered to a user with the aerosol generating device 120.

For deep lung penetration, a preferred embodiment of the aerosol confinement sleeve 140 can be configured to provide aerosol particles having a mass median aerodynamic diameter in a range between about 0.2 microns to about 0.5 microns. If central lung deposition is desired, the aerosol confinement sleeve 140 can be configured to provide aerosol particles having a mass median aerodynamic diameter in a range between about 1 micron and about 2 microns. Furthermore, if deposition in the upper respiratory tract for medicaments, such as bronchodilators, is desired, a larger particle size can be delivered by an appropriate configuration of the aerosol confinement sleeve 140.

In a preferred embodiment, the aerosol confinement sleeve 140 is removably attached to the body 129 by any suitable connection (e.g., a threaded connection, snap-fit connection, or friction fit) so that one aerosol confinement sleeve may be interchanged with a different aerosol confinement sleeve having a different configuration in order to deliver aerosols having a different size distribution using the same capillary passage 128 and heater. Therefore, the aerosol generating device 120 may be adaptable for different targeted aerosol depositions for users. Such interchangeability of the aerosol confinement sleeve is also useful in laboratory aerosol generating devices used to study aerosol formation, or in commercial devices in which a certain aerosol particle size may be desired.

In a preferred embodiment, the body 129 can have approximately the same inner diameter as the aerosol confinement sleeve 140. In another preferred the body 129 can have a different (e.g., larger) inner diameter than the aerosol confinement sleeve 140.

To further illustrate, if a user having the aerosol generating device 120 configured for lung delivery of an aerosol desires to use the aerosol generating device 120 for upper respiratory tract delivery, which utilizes a larger aerosol particle size, the aerosol confinement sleeve 140 configured for lung penetration can be replaced with one configured for upper respiratory tract aerosol delivery.

As shown in FIG. 1, the aerosol confinement sleeve 140 can extend into the space 132b of the mouthpiece 132. Depending on the length L of the aerosol confinement sleeve 140, the location of the outlet of the aerosol confinement sleeve in the space 132b can be selectively varied.

As depicted in FIG. 2, volatilized material 143 exiting the flow passage 128 enters the interior space 142 of the aerosol confinement sleeve 140. Air in the interior space 142 admixes with the volatilized material, which forms an aerosol, such as a condensation aerosol, when the vapor is cooled by the air. The aerosol exits from the outlet end of the aerosol confinement sleeve 140 and is inhaled by a user drawing on the mouthpiece 132.

As described further below, it has been determined that for a given dimension W of the aerosol confinement sleeve 140, increasing the length L of the aerosol confinement sleeve 140 increases the size of aerosol particles produced with the aerosol generating device. It has further been determined that by decreasing the dimension W of the aerosol confinement sleeve, the length L of the aerosol confinement sleeve for producing a selected aerosol size is decreased. Accordingly, the length L and dimension W can be selectively varied to produce aerosols having selected particle sizes.

The source 122 may contain a suitable liquid aerosol formulation, such as a solution or suspension of a carrier and one or more other components, depending on the intended application of the aerosol. For example, the carrier can be water and/or propylene glycol (PG). In a preferred embodiment, the liquid aerosol formulation includes a liquid carrier and a liquid and/or particulate medicament. The medicament can be any suitable medicament that can be delivered via an aerosol. For example, suitable medicaments include, but are not limited to, analgesics, anginal preparations, anti-allergics, antibiotics, antihistamines, antitussives, bronchodilators, diuretics, anticholinergics, hormones, and anti-flammatory agents, such as those described in U.S. Pat. No. 6,153,173, which is incorporated herein by reference in its entirety. The liquid aerosol formulation can be selected to provide a desired dose of the medicament via aerosol inhalation.

However, the liquid aerosol formulation does not have to include a medicament. For example, the liquid aerosol formulation may include substances, such as paints, scents, or fuels for research, commercial or industrial applications.

EXAMPLES

The following examples demonstrate features of the invention. The examples are not intended to and should not be interpreted as limiting the invention.

Example 1

Figure 3:
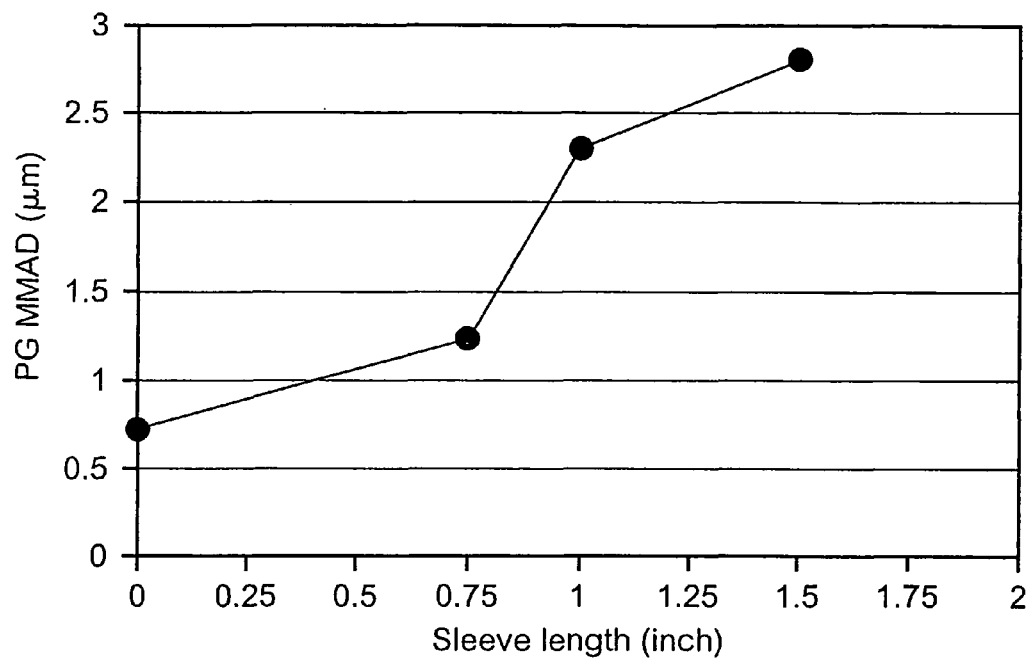
FIG. 3 shows the relationship between the mass median aerodynamic diameter (MMAD) of propylene glycol (PG) and the aerosol confinement sleeve length.
Figure 4:
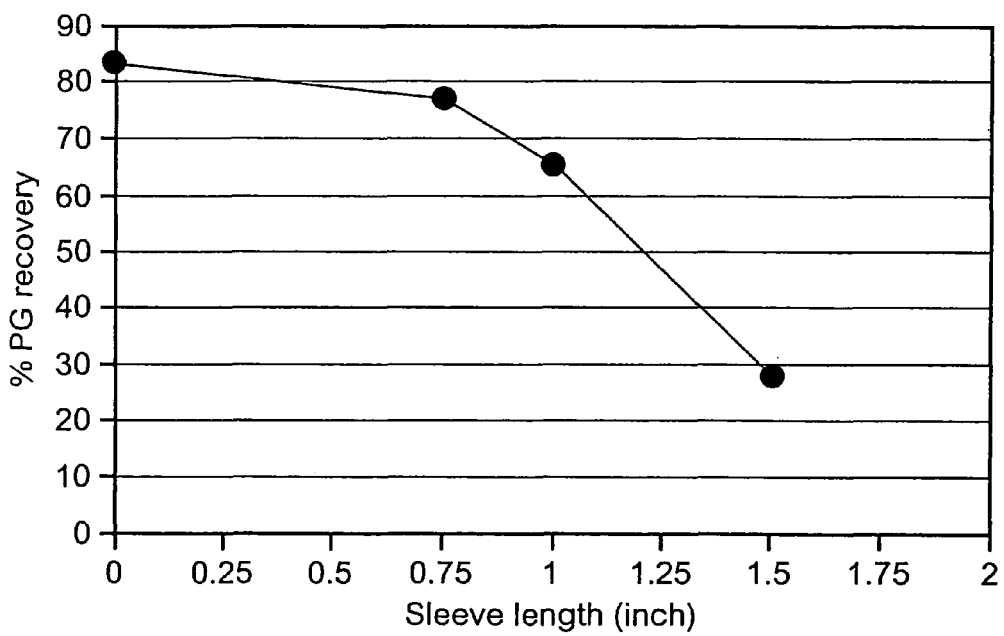
FIG. 4 shows the relationship between the percentage PG recovery and the aerosol confinement sleeve length.

Tests were conducted to demonstrate the effect of an aerosol confinement sleeve on aerosol particle size and the percent recovery of a liquid aerosol formulation. The arrangement tested included a cylindrical, plastic body surrounding a flow passage heated by a 28 gauge/44 mm CTP heater. The body had a ⅜ inch inner diameter and a ½ inch outer diameter. Three cylindrical aerosol confinement sleeves each having a ½ inch inner diameter, but having different lengths of 0.75 inch, 1 inch and 1.5 inch, were separately fitted on the body. An aerosol was produced using PG for the different arrangements. The body was constructed to prevent air flow into the upstream end of the space between the body and the flow passage. For comparative purposes, in one test an aerosol confinement sleeve was not used. The aerosols produced during the four tests were collected in a cascade impactor (model MOUDI from MSP Corporation, Minneapolis, Minn.). As shown in FIG. 3, the aerosol confinement sleeves increased the MMAD of PG from about 0.75 microns (for the comparative example having no aerosol confinement sleeve) to about 2.75 microns for the aerosol confinement sleeve length of 1.5 inch. The aerosol was analyzed to determine the percentage recovery of PG. As shown in FIG. 4, the PG recovery decreased with increasing aerosol confinement sleeve length. This result is attributed to increased deposition of PG on the inner surface of the aerosol confinement sleeve. The test results show that an approximately three-fold increase in the MMAD can be achieved at a recovery of about 65% when using the aerosol confinement sleeve.

Example 2

Figure 5:
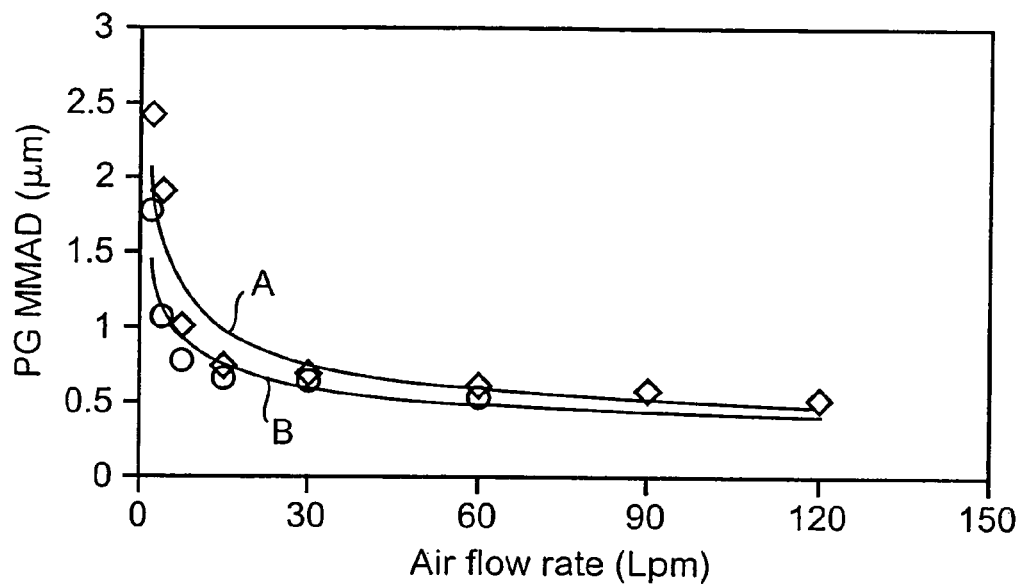
FIG. 5 shows the relationship between the MMAD of PG aerosol particles and the air flow rate (inhalation rate) for two different sized capillary passages.

Tests were conducted to determine the effect of the inhalation flow rate of a user on the MMAD of aerosol particles generated from propylene glycol (PG) supplied at a flow rate of 5 mg/sec with an aerosol generating device. Two cylindrical air intake passages supplying air to the mouthpiece having respectively different inner diameters of ⅞ inch and ¼ inch were used. Different users of an aerosol generating device, such as the aerosol generating device 120, are expected to inhale on the mouthpiece at different air flow rates. The test results are shown in FIG. 5, in which Curve A represents the results for the air intake passage having a ⅞ inch inner diameter, and Curve B the results for the air intake passage having a ¼ inch inner diameter. The results in Curves A and B demonstrate that the inhalation flow rate (air flow rate) of a user can significantly affect the MMAD of aerosol particles at low air flow rates (i.e., less than about 15 Lpm), but that the MMAD is relatively independent of the air flow rate over a range of values from about 15 Lpm to about 120 Lpm. Comparing Curves A and B, it can be seen that the MMAD of PG was higher at a given air flow rate for the air intake passage having the larger inner diameter. The air flow rate range of about 15 Lpm to about 120 Lpm is expected to be broader than that employed by users. The increase in the MMAD of PG at lower air flow rates is believed to be due to the decreased rate of cooling of the vapor emitted from the flow passage under these conditions. This phenomena can be employed to produce larger aerosol particle distributions suitable for targeted deposition in the upper respiratory tract.

Example 3

Figure 6:
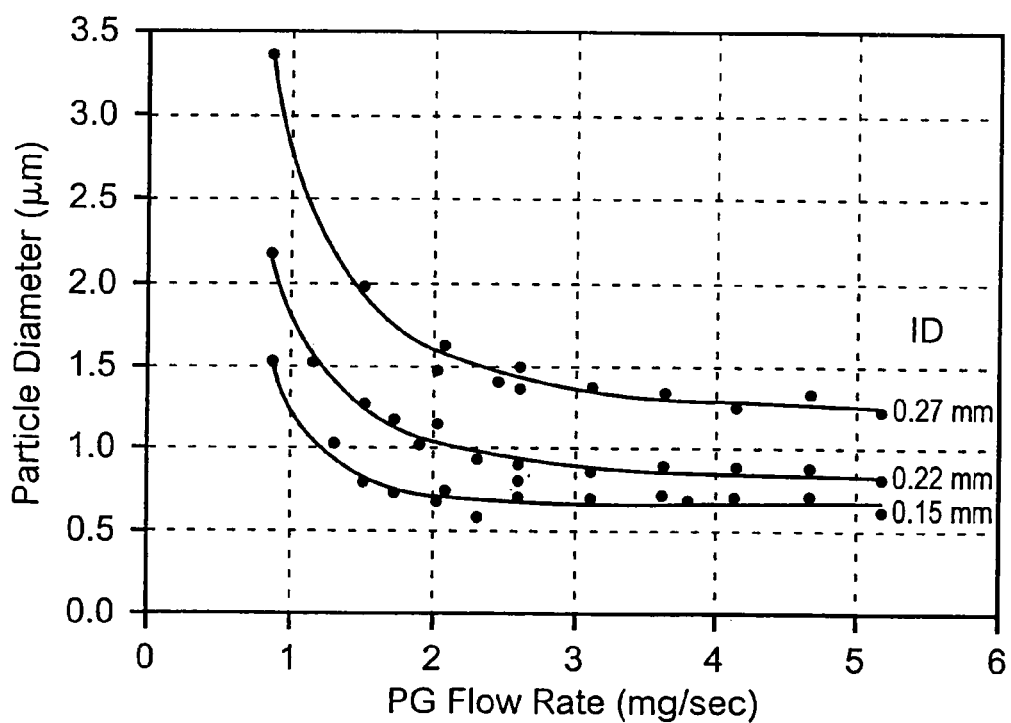
FIG. 6 illustrates the relationship between aerosol particle diameter and PG flow rate in the flow passage for aerosols produced using different sized flow passages.

Tests were conducted to demonstrate the effect of the aerosol liquid flow rate in the capillary passage and the size of the capillary passage on the size of aerosol particles produced. As shown in FIG. 6, three different capillary passages having inner diameters of 0.27 mm, 0.22 mm and 0.15 mm, respectively, were used to produce aerosols from PG at PG flow rates from about 0.75 mg/sec to about 5.25 mg/sec in the capillaries. The MMAD of aerosol particles was increased by increasing the inner diameter of the capillary passage. The effect of the aerosol liquid flow rate is small at higher flow rates. Accordingly, these test results demonstrate that the capillary size is a more important control parameter with respect to aerosol particle size than the liquid flow rate in the capillary passage.

Example 4

Figure 7:
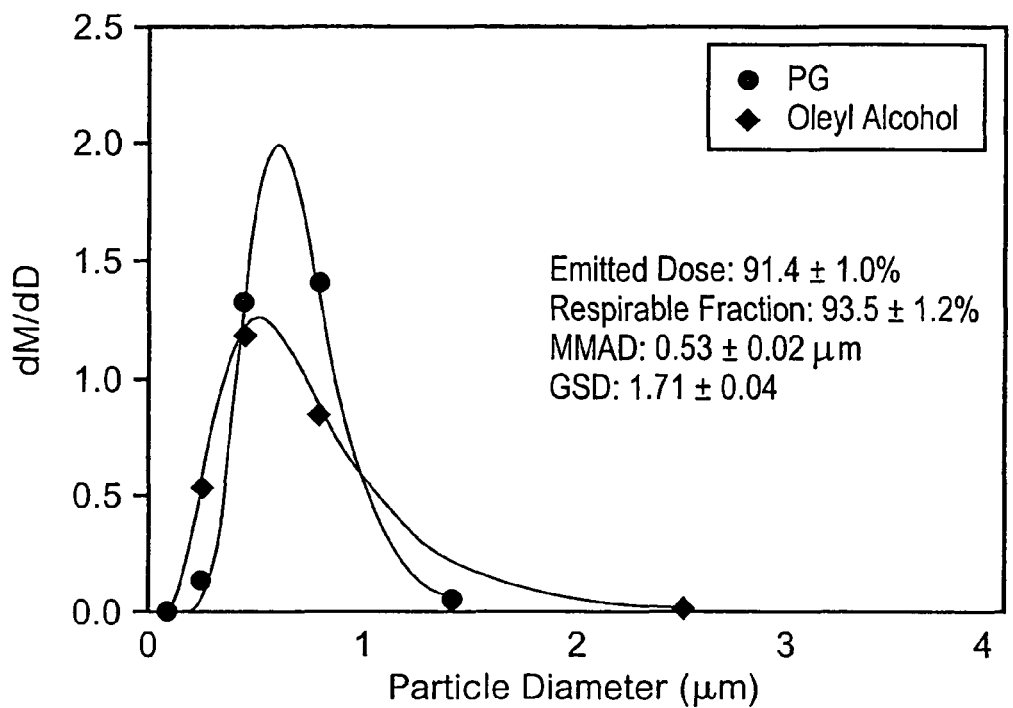
FIG. 7 shows the size distributions of aerosol particles of PG and oleyl alcohol (OA) in an aerosol produced from a solution of OA in PG.

An aerosol was produced using an aerosol generating device from a PG/5% oleyl alcohol (OA) solution. The size distribution of the aerosol particles was determined using a cascade impactor. As shown in FIG. 7, the resulting aerosol included particles of PG and OA, which had respectively different particle size distributions from each other.

Example 5

Figure 8:
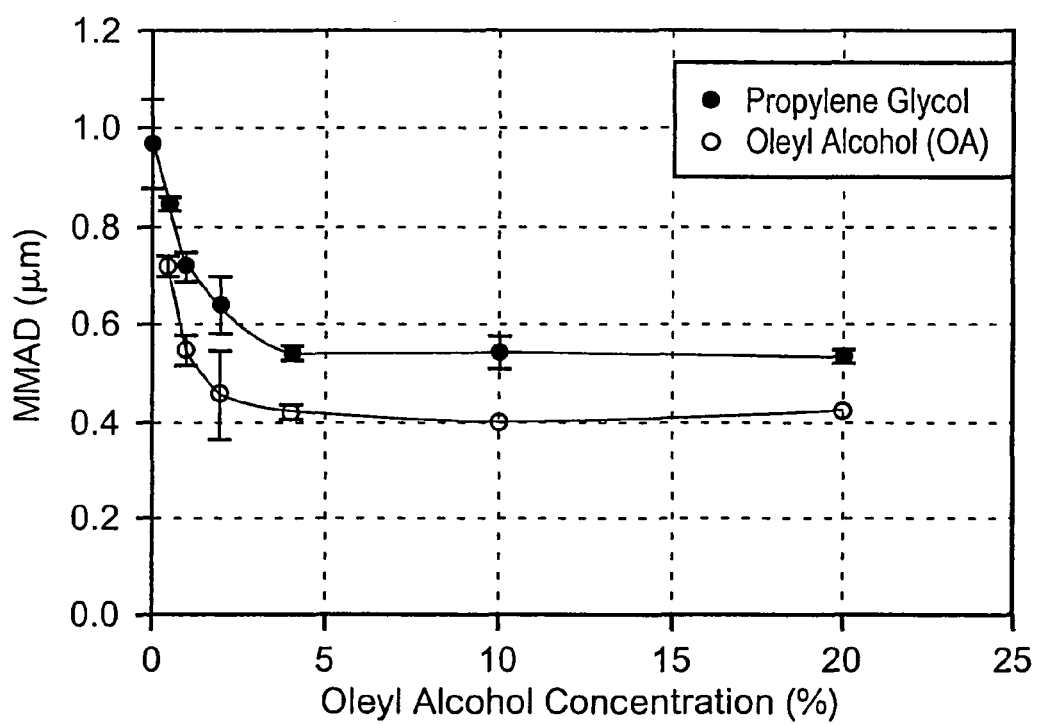
FIG. 8 shows the MMAD of aerosol particles of PG and OA in aerosols produced from solutions having different concentrations of OA in PG.

Aerosols were produced using an aerosol generating device from PG/OA solutions having different concentrations of OA. FIG. 8 illustrates the relationship between the MMAD of aerosolized PG and aerosolized OA in the different aerosols. The size distribution of the aerosol particles of PG and OA was determined using a cascade impactor. The effect of the OA concentration on the MMAD of both PG and OA was more significant at lower OA concentrations than at higher concentrations. These results show that aerosol particle size can be affected by the solute concentration of the liquid used to produce the aerosol. In addition, the test results show that aerosol particles having an MMAD of 0.4-1.2 microns can be achieved.

Example 6

Figure 9:
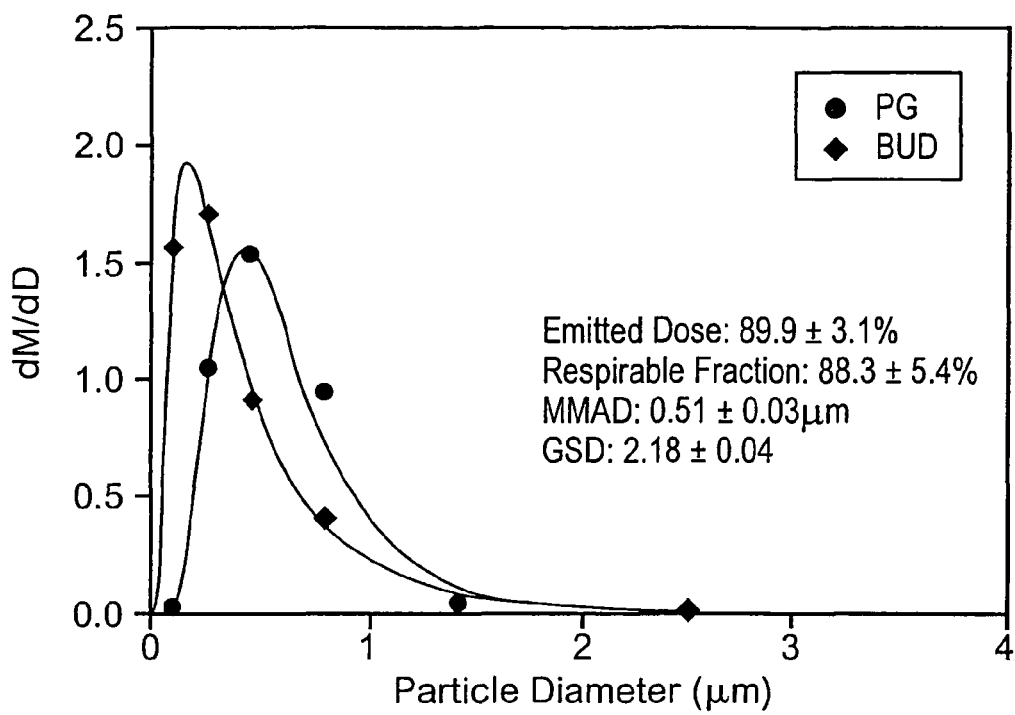
FIG. 9 shows the size distribution of aerosol particles of budesonide and PG in an aerosol produced from a solution of budesonide in PG.

A test was conducted to generate an aerosol from a solution of another low volatility carrier and solute. A 1% solution of budesonide in PG was vaporized in an aerosol generating device and admixed with ambient air. The measured size distributions of the aerosol particles of budesonide and PG are shown in FIG. 9.

Example 7

Figure 10:
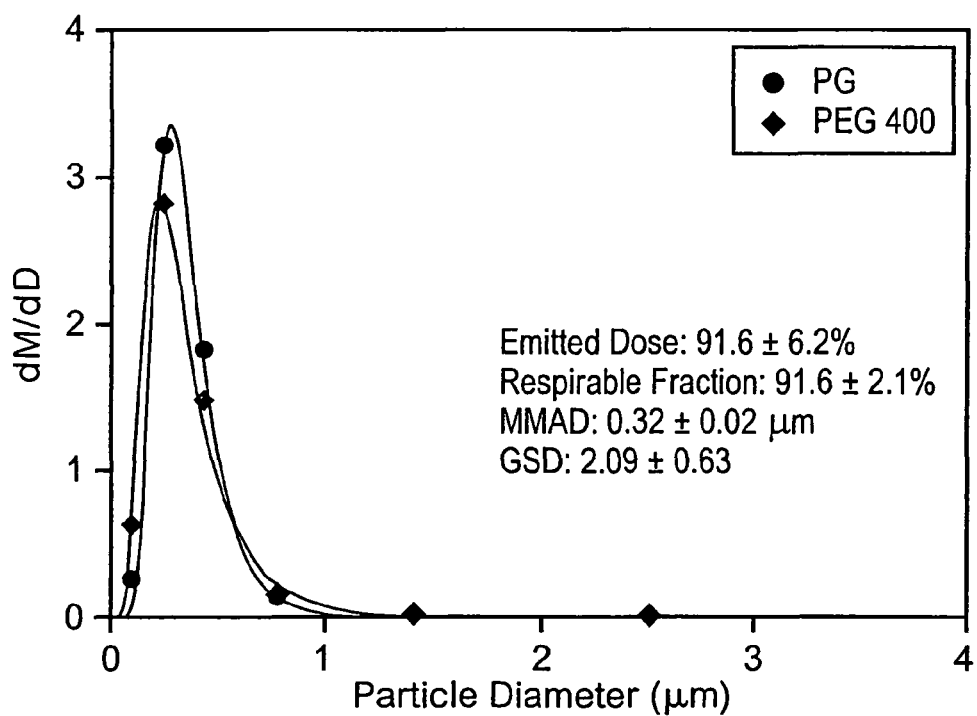
FIG. 10 shows the size distribution of aerosol particles of PEG 400 and PG in an aerosol produced from a solution of PEG 400 in PG.

A test was conducted to generate an aerosol from a solution of PG and another solute. A 1% solution of PEG 400 (a polyethylene glycol having a molecular weight of 400 g/mole) in PG was vaporized in an aerosol generating device and admixed with ambient air. The measured size distributions of the aerosol particles of PEG 400 and PG are shown in FIG. 10.

Example 8

Tests were conducted to study the variation in the MMAD of PG aerosol particles versus the aerosol confinement sleeve length, which ranged from 0.5 inch to 1.5 inch. The confinement sleeve inner diameter was 0.5 inch for each of the different sleeve lengths. A 28 gauge/44 mm long controlled temperature profile (CTP) heater was used at a 5 mg/sec PG flow rate. Capillaries having a controlled temperature profile construction are described in commonly-assigned U.S. application Ser. No. 09/957,026, filed on Sep. 21, 2001, which is incorporated herein by reference in its entirety. The aerosol generated was collected with a mouthpiece having an inner diameter of 1.25 inch. The mouthpiece was arranged downstream of, in flow communication with, the aerosol confinement sleeve. The aerosol confinement sleeve and the mouthpiece were concentrically arranged so that an annular space existed between the outer surface of the aerosol confinement sleeve and the inner surface of the mouthpiece. Air was drawn into the annular space and mixed with aerosol exiting the aerosol confinement sleeve. Triplicate tests were performed for each confinement sleeve length. Percent PG recovery was measured under approximate steady-state conditions using a MOUDI cascade impactor.

Figure 11:
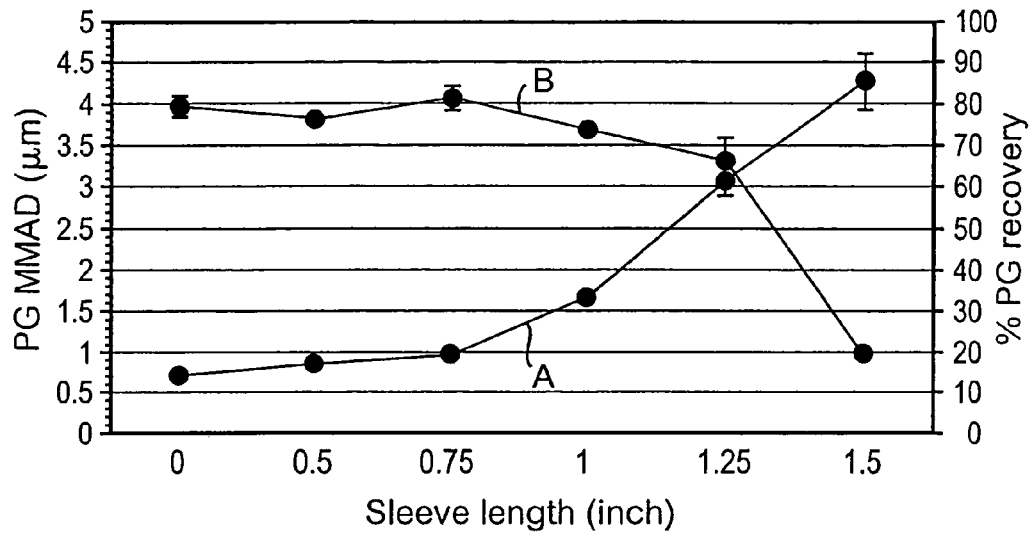
FIG. 11 shows relationships between the MMAD of PG aerosol particles and aerosol confinement sleeve length (Curve A), and between percent PG recovery and aerosol confinement sleeve length (Curve B) for a mouthpiece having an inner diameter of 1.25 inch.

FIG. 11 shows the MMAD of PG aerosol particles (Curve A) and percent PG recovery (Curve B) versus aerosol confinement sleeve length. As shown, there is about a two-, four-, and six-fold increase in particle size (from a reference value of 0.7 µm without a sleeve) for the sleeve lengths of 1 inch, 1.25 inch and 1.5 inch, respectively. Percent PG recoveries are about 73%, 66% and 19% for the confinement sleeve lengths of 1 inch, 1.25 inch and 1.5 inch, respectively.

Example 9

Figure 12:
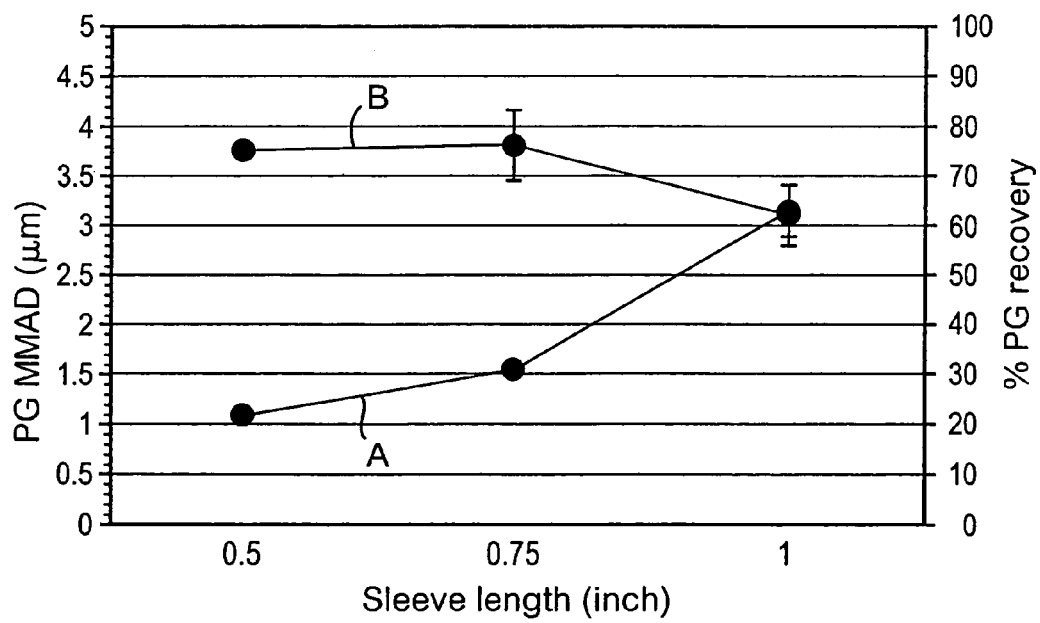
FIG. 12 shows relationships between the MMAD of PG aerosol particles and aerosol confinement sleeve length (Curve A), and between percent PG recovery and aerosol confinement sleeve length (Curve B) for a mouthpiece having an inner diameter of ⅞ inch.

The effect of the mouthpiece inner diameter on aerosol particle size was measured using a 22 mm (⅞ inch) inner diameter mouthpiece arranged co-axially with aerosol confinement sleeves having a length of 0.5 inch, 0.75 inch, and 1 inch. The PG flow rate was 5 mg/sec. In FIG. 12, Curve A shows the MMAD of PG aerosol particles, and Curve B shows the percent PG recovery. A four-fold aerosol particle size growth was observed for a sleeve length of 1 inch with a recovery of about 62%. Comparing FIG. 11 (Example 8), a similar four-fold growth with a recovery of about 66% was also observed for a longer aerosol confinement sleeve length of 1.25 inch.

Figure 13:
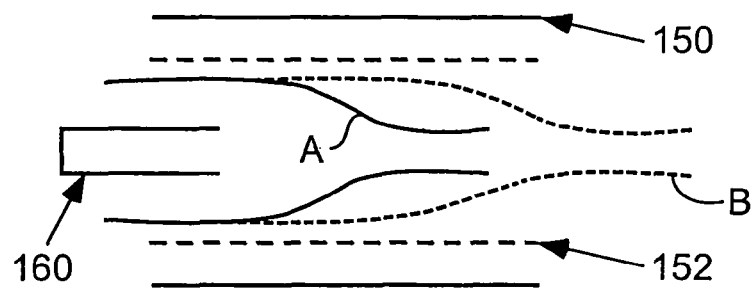
FIG. 13 shows approximated air streamlines generated with mouthpieces having an inner diameter of 1.25 inch (A) and ⅞ inch (B).
Figure 14:
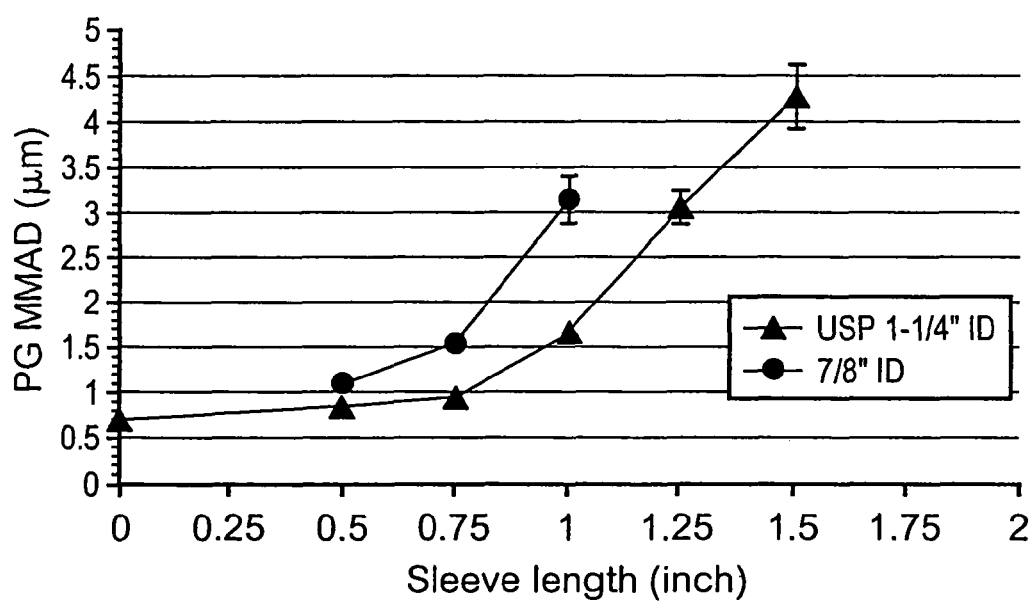
FIG. 14 shows the relationship between the MMAD of PG aerosol particles and aerosol confinement sleeve length for mouthpieces having an inner diameter of 1.25 inch and ⅞ inch.

A possible explanation for the difference in the results shown in FIGS. 11 and 12 is depicted in FIG. 13. In FIG. 13, A and B represent approximated air streamlines for the mouthpiece 150 having an inner diameter of 1.25 inch and the mouthpiece 152 having an inner diameter of ⅞ inch, respectively, disposed coaxially with a flow passage/aerosol confinement sleeve 160. Streamline B representing the smaller-inner diameter mouthpiece is based on a higher air velocity between the aerosol confinement sleeve and the mouthpiece 152, which increases the length of the core region between the streamlines A and B where mixing occurs at a slower rate. Streamline A representing the larger mouthpiece indicates that mixing and dilution are expected to be significantly faster due to a smaller core region, resulting in a smaller particle size. This is shown in FIG. 14, which combines Curve A of FIG. 11 and curve A of FIG. 12. As shown in FIG. 14, at a given sleeve length, the MMAD of PG aerosol particles is smaller for the mouthpiece having a 1.25 inch inner diameter than for the mouthpiece having a ⅞ inch inner diameter.

Example 10

Figure 15:
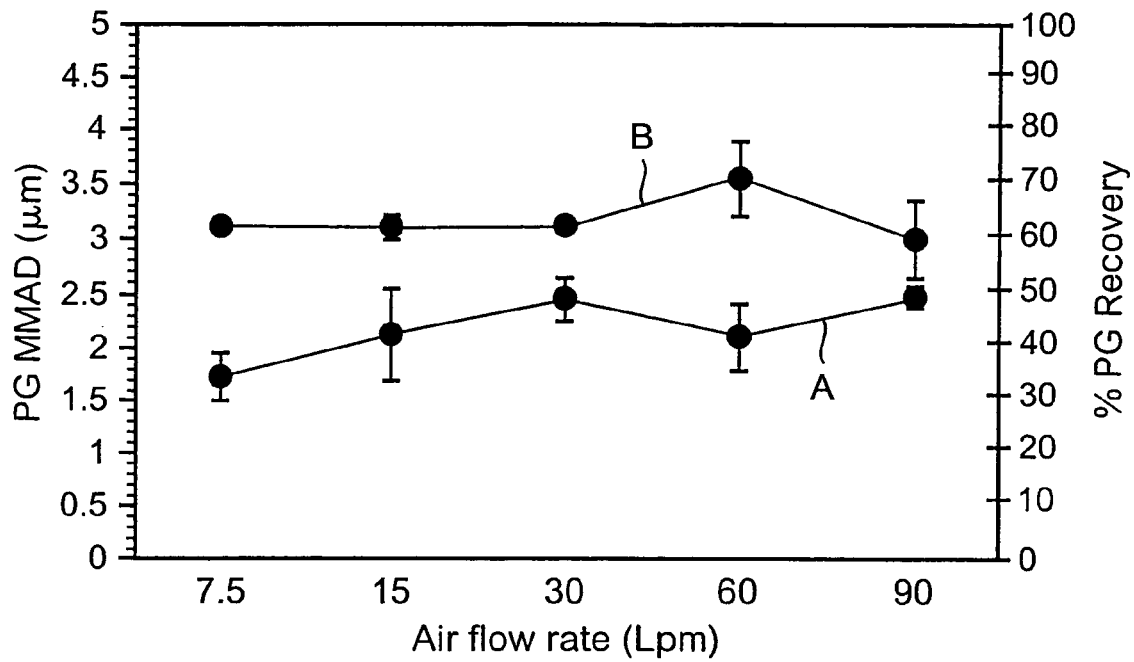
FIG. 15 shows relationships between the MMAD of PG aerosol particles and air flow rate (Curve A), and between percent PG recovery and air flow rate (Curve B) for a mouthpiece having an inner diameter of ¾ inch.

A mouthpiece having an inner diameter of ¾ inch, and an aerosol confinement sleeve having a ½ inch inner diameter and a length of ¾ inch were used. The results are shown in FIG. 15. As shown in Curve A, there was no significant difference in the MMAD of PG aerosol particles over the flow rate range of 15 Lpm to 90 Lpm. The values for percent PG recovery shown in Curve B are based on the amount in the impactor and under approximate steady state conditions.

Example 11

Figure 16:
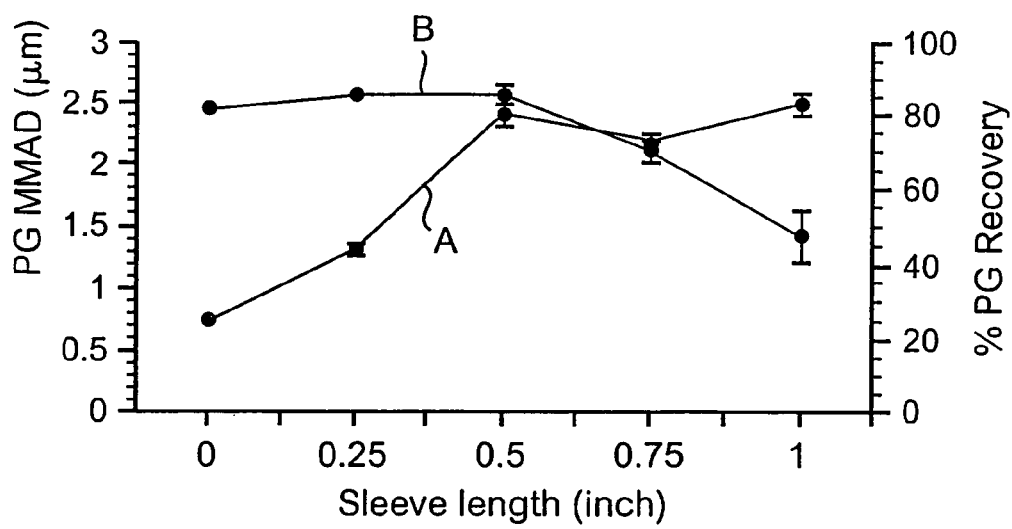
FIG. 16 shows relationships between the MMAD of PG aerosol particles and aerosol confinement sleeve length (Curve A), and between percent PG recovery and aerosol confinement sleeve length (Curve B) for an aerosol confinement sleeve having an inner diameter of ⅜ inch for a PG flow rate of 10 mg/sec.

An aerosol generator was tested using an aerosol confinement sleeve with a ⅜ sleeve inner diameter at a higher PG flow rate of 10 mg/sec. FIG. 16 shows plots of the MMAD of the PG aerosol particles (Curve A), and percent PG recovery (Curve B, filter capture method) versus the aerosol confinement sleeve length. Two replicate tests were performed for each data point. FIG. 16 shows that about a two- and three-fold growth in the PG MMAD can be achieved with ¼ inch and ½ inch long aerosol confinement sleeves, respectively. The percent PG recovery was relatively constant at about 85% up to a sleeve length of ½ inch.

Figure 17:
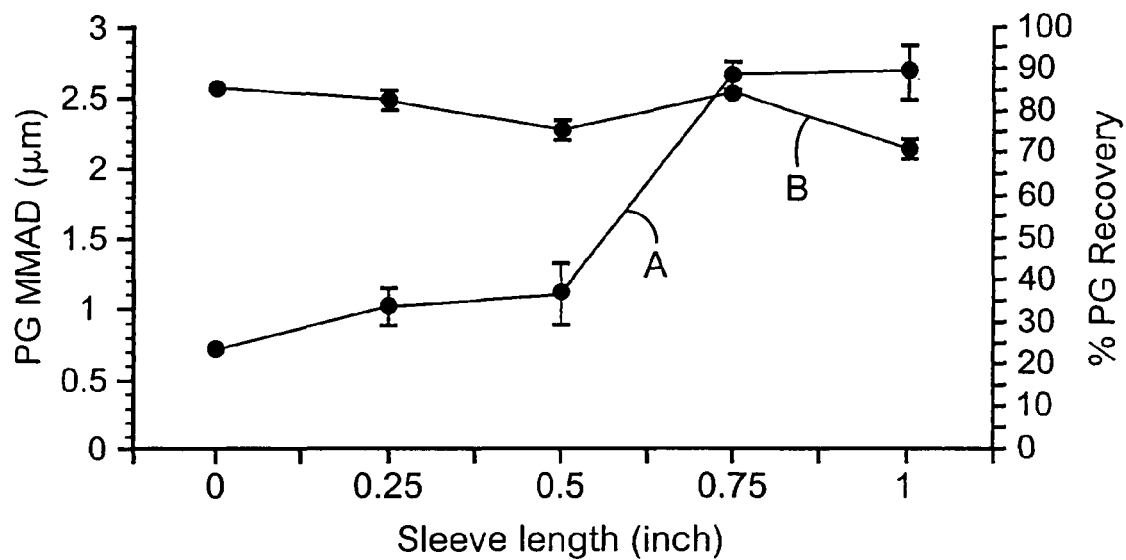
FIG. 17 shows relationships between the MMAD of PG aerosol particles and aerosol confinement sleeve length (Curve A), and between percent PG recovery and aerosol confinement sleeve length (Curve B), for an aerosol confinement sleeve having an inner diameter of ⅜ inch and a PG flow rate of 5 mg/sec.

FIG. 17 shows results for the same test configuration, but at a lower PG flow rate of 5 mg/sec. As shown in Curve A, PG aerosol particle growth is lower for the ¼ inch and ½ inch aerosol confinement sleeves than at 10 mg/sec (see FIG. 16). However, the MMAD of PG aerosol particles levels off at about 2.7 μm for the longer aerosol confinement sleeve lengths of 0.75 inch and 1 inch.

Example 12

Example 12 demonstrates the use of an aerosol confinement sleeve having a smaller ¼ inch inner diameter as compared to an aerosol confinement sleeve inner diameter of ⅜ inch used in Example 11. The ¼ inch inner diameter sleeves snap on to the end of the body of the aerosol generator and have about the same inner diameter and outer diameter as the body. The PG mass flow rate was 10 mg/sec and the collection air flow rate was 30 Lpm.

Figure 18:
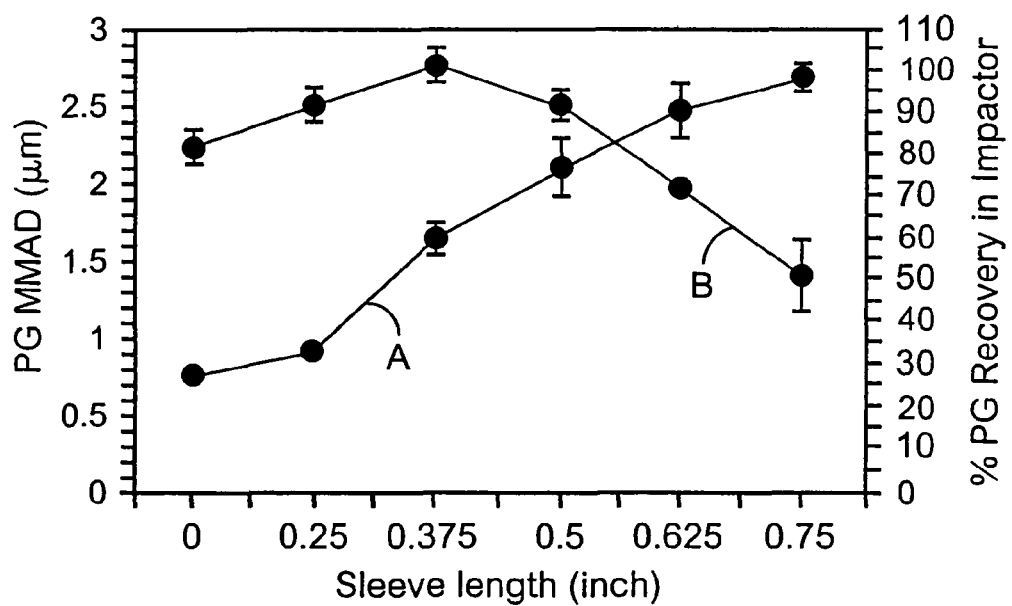
FIG. 18 shows relationships between the MMAD of PG aerosol particles and aerosol confinement sleeve length (Curve A), and between percent PG recovery and aerosol confinement sleeve length (Curve B) for an aerosol confinement sleeve having an inner diameter of ¼ inch and at a PG flow rate of 10 mg/sec.

FIG. 18 shows the MMAD of PG aerosol particles (Curve A) and percent PG recovery (Curve B) by aerosol mass in the MOUDI cascade impactor. An MMAD of PG aerosol particles of about 2.5 μm can be achieved with an aerosol confinement sleeve length of ⅝ inch with a PG recovery of about 70% in the impactor. This is more than a three-fold growth in aerosol particle size. Triplicate runs were performed for each confinement sleeve length.

Example 13

Figure 19:
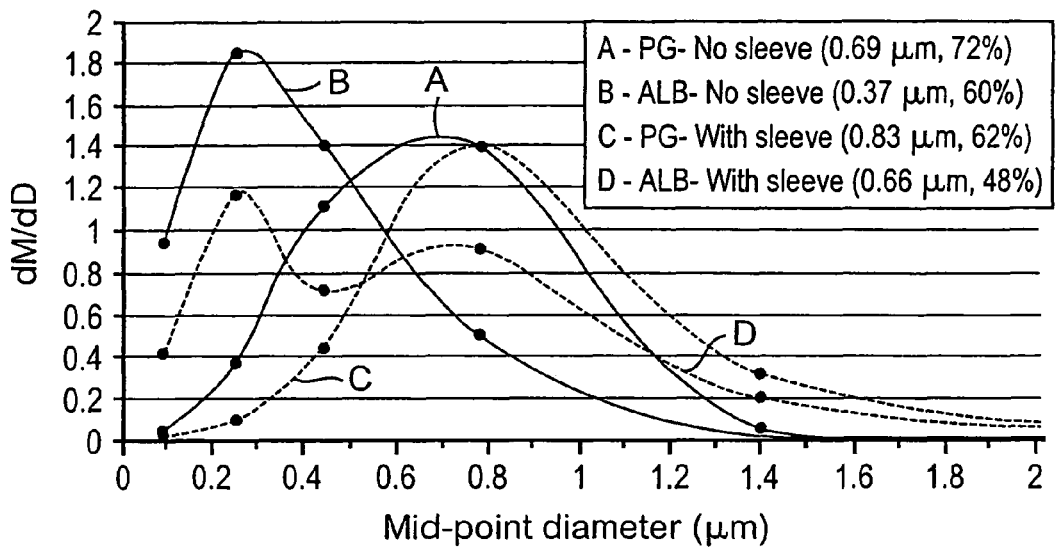
FIG. 19 shows size distributions for PG aerosol particles (Curve C) and albuterol aerosol particles (Curve D) produced with a 1% w/w albuterol in PG solution with an aerosol confinement sleeve, and for PG aerosol particles (Curve A) and albuterol aerosol particles (Curve B) produced without the aerosol confinement sleeve.

The effect on aerosol particle size of an aerosol confinement sleeve for a medicament (albuterol) dissolved in PG was tested with a 1% w/w albuterol in PG solution. FIG. 19 shows the aerosol particle size distributions for PG and albuterol aerosol particles generated using an aerosol confinement sleeve having a ½ inch length and ¼ inch inner diameter (Curves C and D, respectively) and without an aerosol confinement sleeve (Curves A and B, respectively) at a formulation flow rate at 10 mg/sec. Without the confinement sleeve, the MMAD of PG aerosol particles was 0.69 μm and the MMAD of albuterol aerosol particles was 0.37 μm. Both components fit a uni-modal lognormal distribution. With the confinement sleeve, the MMAD of PG aerosol particles increased to 0.83 μm and maintained its log-normality (Curve C). In contrast, the albuterol aerosol particle size distribution became bi-modal with an MMAD value of 0.66 μm (Curve D). The percentage recovery values of 72%, 60%, 62%, and 48% shown in FIG. 19 are based on the mass collected in a cascade impactor. These test results with a two-component liquid system show that the aerosol confinement sleeve can enhance aerosol particle growth of both components.

Example 14

Figure 20:
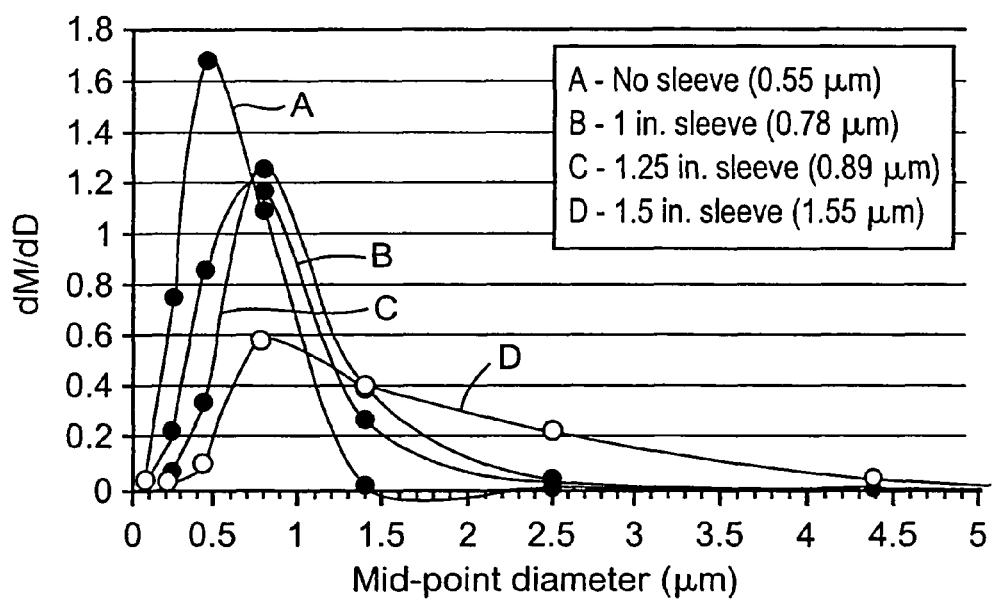
FIG. 20 shows PG total aerosol particle size distributions produced with a 0.5% w/w albuterol in PG solution without an aerosol confinement sleeve (Curve A), and produced with an aerosol confinement sleeve having a length of 1 inch (Curve B), 1.25 inch (Curve C), and 1.5 inch (Curve D).

The effect on aerosol particle size for a medicament dissolved in PG was tested with a lower 0.5% w/w albuterol in PG solution, and at a flow rate of 5 mg/sec. FIG. 20 shows the PG (total) aerosol particle size distribution without an aerosol confinement sleeve (Curve A), and with confinement sleeves having a length of 1 inch (Curve B), 1.25 inch (Curve C), and 1.5 inch (Curve D).

Referring to FIG. 20, the MMAD of PG aerosol particles increases from 0.55 μm without a confinement sleeve to 1.55 μm with a 1.5 inch long sleeve. This represents about a three-fold growth in PG aerosol particle size. Table 1 below shows that impactor recovery (gravimetric) of PG is 79% for the 1.5 inch long confinement sleeve.

Figure 21:
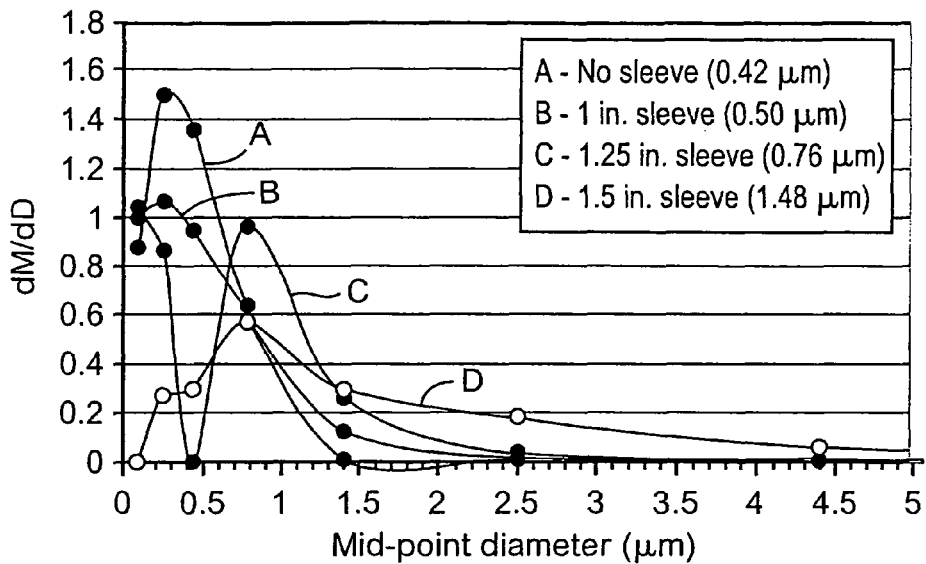
FIG. 21 shows albuterol aerosol particle size distributions produced with a 0.5% w/w albuterol in PG solution without an aerosol confinement sleeve (Curve A), and produced with an aerosol confinement sleeve having a length of 1 inch (Curve B), 1.25 inch (Curve C), and 1.5 inch (Curve D).

FIG. 21 shows the size distributions for the albuterol aerosol particles for the 0.5% w/w albuterol in PG solution. The MMAD of albuterol aerosol particles increases from 0.42 μm without a sleeve to 1.48 μm with a 1.5 inch long sleeve. This represents a 3.5-fold growth in albuterol particle size. Impactor recovery of albuterol was 79% without a confinement sleeve, and about 50% with the 1.5 inch long confinement sleeve.

TABLE 1

| Sleeve Length | TOTAL (PG) | | ALBUTEROL | |
|---|---|---|---|---|
| | MMAD | Recovery | MMAD | Recovery |
| None | 0.55 μm | 101% | 0.42 μm | 79% |
| 1.00 in | 0.78 μm | 74% | 0.50 μm | 50% |
| 1.25 in | 0.89 μm | 88% | 0.76 μm | 57% |
| 1.50 in | 1.55 μm | 79% | 1.48 μm | 50% |

Example 15

In the Examples described above, aerosol confinement sleeves were evaluated for aerosol particle size control with PG as the carrier. In Example 15, the ability of the confinement sleeves having an inner diameter of ½ inch to enhance aerosol particle growth with a different carrier liquid, triacetin (glyceryl triacetate), was evaluated. A 28 gauge/44 mm long CTP heater was used at a triacetin flow rate of 5 mg/sec. Duplicate runs were conducted for each confinement sleeve length. The gravimetric method was used to measure the mass of triacetin on each impactor stage. The confinement sleeves had a ½ inch inner diameter and varying lengths.

Figure 22:
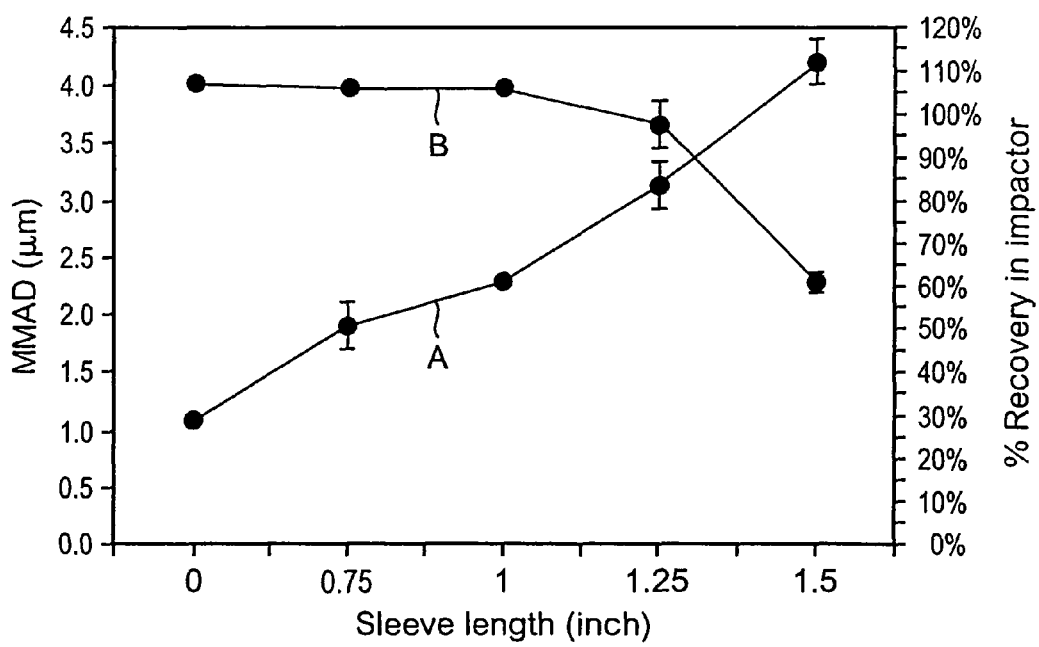
FIG. 22 shows relationships between triacetin aerosol particle size and aerosol confinement sleeve length (Curve A), and between triacetin recovery and aerosol confinement sleeve length (Curve B) for an aerosol confinement sleeve having an inner diameter of 0.5 inch.

As shown in FIG. 22, without an aerosol confinement sleeve, the MMAD of triacetin aerosol particles is about 1 µm (Curve A). With a ¾ inch long aerosol confinement sleeve, the aerosol particle size almost doubled with no significant change in impactor recovery. With a 1.25 inch long aerosol confinement sleeve, there was a three-fold growth in the MMAD of triacetin aerosol particles with a recovery greater than 95% (Curve B). For the longest aerosol confinement sleeve length tested (1.5 inch), there was a four-fold growth in aerosol particle size, but the recovery dropped to about 60%. The overall trends in particle growth and recovery of triacetin are similar to those observed for PG.

Example 16

Figure 23:
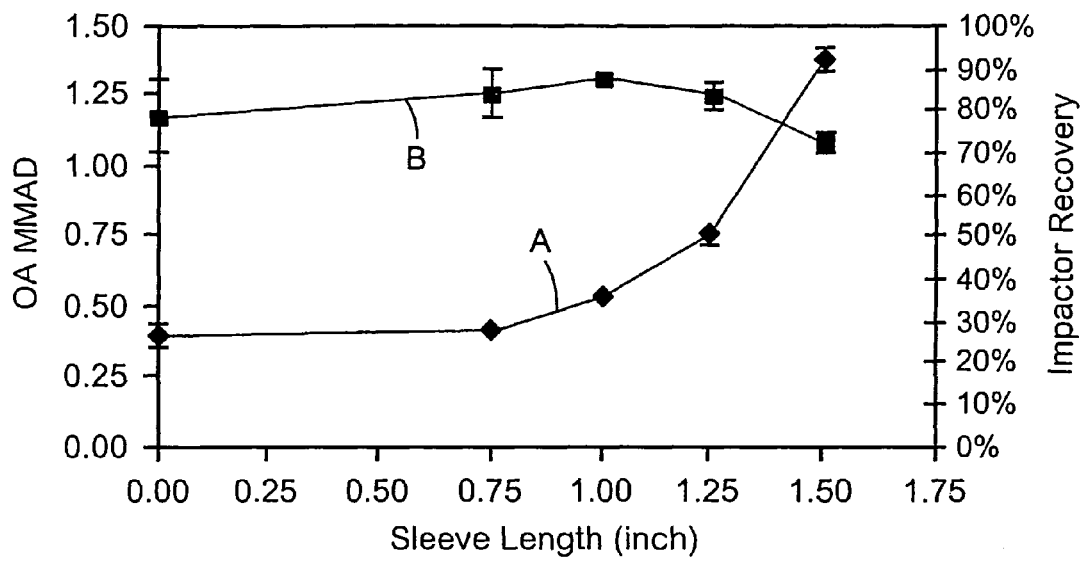
FIG. 23 shows relationships between the MMAD of OA aerosol particles and aerosol confinement sleeve length (Curve A), and between percent PG recovery and aerosol confinement sleeve length (Curve B) for a 5% w/w OA in PG solution and using an aerosol confinement sleeve having a ½ inch inner diameter.

A solution of 5% w/w OA in PG was used as another two-component system. A 28 gauge/44 mm long CTP heater was used at a formulation flow rate of 5 mg/sec. FIG. 23 shows the MMAD of OA aerosol particle (Curve A) and percent recovery of OA (Curve B) in the impactor for OA versus the aerosol confinement sleeve length. The confinement sleeves had a ½ inch inner diameter and lengths of ¾ inch, 1 inch, 1.25 inch, and 1.5 inch. Without a sleeve, the average MMAD of OA aerosol particles was 0.39 µm with an impactor recovery of 78%. The MMAD of OA aerosol particles approximately doubled at a confinement sleeve length of 1.25 inch while maintaining a good impactor recovery of 83%. At the longest sleeve length of 1.5 inch, the MMAD of OA aerosol particles increased by a factor of about 3.5 as compared to using no confinement sleeve. Average impactor recovery for the longest confinement sleeve length was 73%, as compared to 78% with no confinement sleeve.

Figure 24:
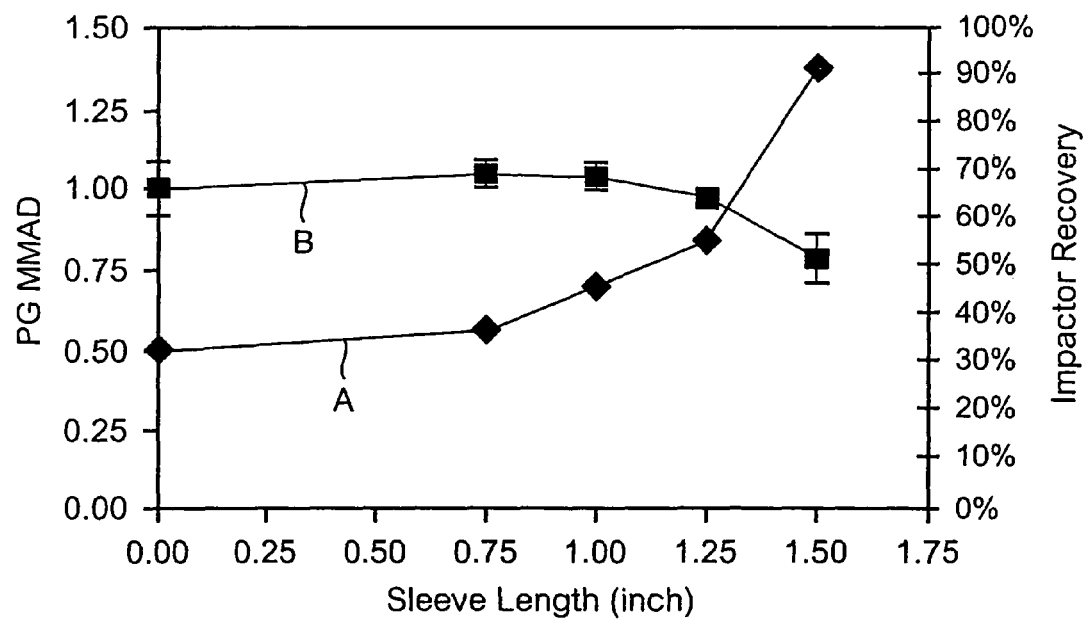
FIG. 24 shows relationships between the MMAD of PG aerosol particles and aerosol confinement sleeve length (Curve A), and between PG recovery and aerosol confinement sleeve length (Curve B) for a 5% w/w OA in PG solution with an aerosol confinement sleeve having a ½ inch inner diameter.

FIG. 24 shows the MMAD of PG aerosol particles (Curve A) and PG recoveries (Curve B) versus the aerosol confinement sleeve length. For the longest confinement sleeve length of 1.5 inch, the growth factor of PG aerosol particles was about 2.7.

Figure 25:
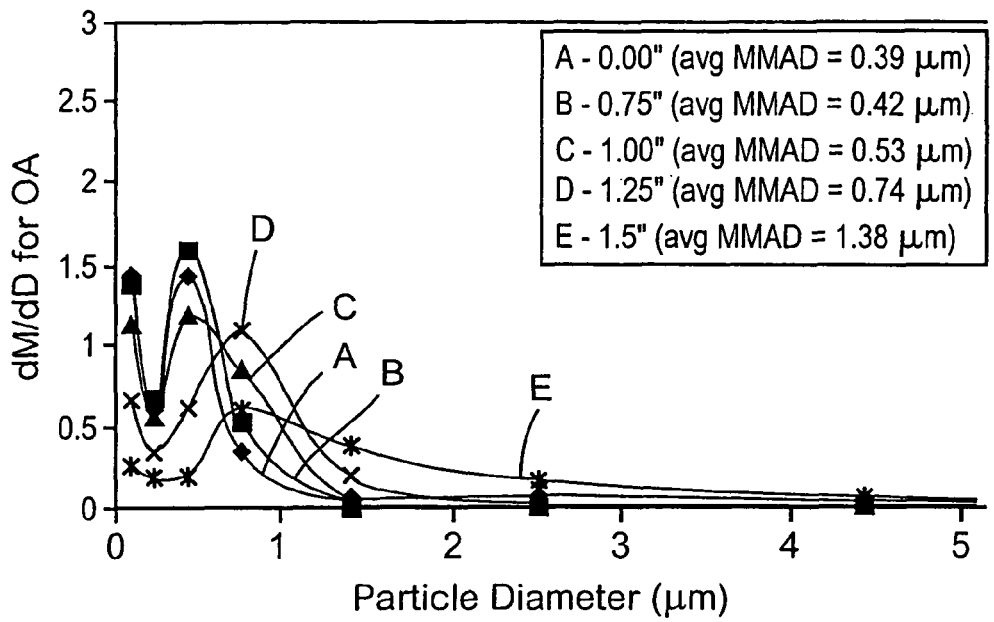
FIG. 25 shows the aerosol particle distribution for OA produced without an aerosol confinement sleeve (Curve A), and produced with an aerosol confinement sleeve having a length of 0.75 inch (Curve B), 1 inch (Curve C), 1.25 inch (Curve D), and 1.5 inch (Curve E).

FIG. 25 shows the aerosol particle size distribution for OA for the different sleeve lengths. The average MMAD of OA aerosol particles increases from 0.39 µm without a confinement sleeve to 1.38 µm with a confinement sleeve length of 1.5 inch, which represents a growth factor of about 3.5. The size distribution for OA aerosol particles with no confinement sleeve is bi-modal with a significant ultrafine or filter fraction. As the confinement sleeve length is increased, the size distribution moves towards uni-modality and a significantly reduced ultrafine fraction. Moreover, at the longest sleeve length of 1.5 inch, the size distributions for OA and PG aerosol particles have a significant overlap.

For the case of OA, total recoveries (impactor+elbow+ sleeve) ranged between 85% and 93% for the different sleeve lengths. The maximum sleeve loss was about 9% for the longest sleeve length of 1.5". Losses in the elbow ranged from 3% to 7%.

Example 17

Example 17 used a 5% w/w OA in PG solution to test the effect of the airflow rate past the flow passage and confinement sleeve. The confinement sleeve length was 1.25 inch and the airflow rate past the sleeve was varied from 15 Lpm to 120 Lpm. The effect of inhalation rate on the MMAD of OA aerosol particles, which was used as a model drug, was investigated. The flow rate of the 5% OA/PG formulation was set at 5 mg/sec. A 22 mm (⅞ inch) inner diameter mouthpiece was used. The MMAD of OA aerosol particles was about 1 µm, which is significantly higher than the 0.74 µm size obtained using a standard elbow (1.25 inch inner diameter) in Example 16. A 28 gauge/44 mm long CTP heater was used. Triplicate runs were performed for each airflow rate condition.

Figure 26:
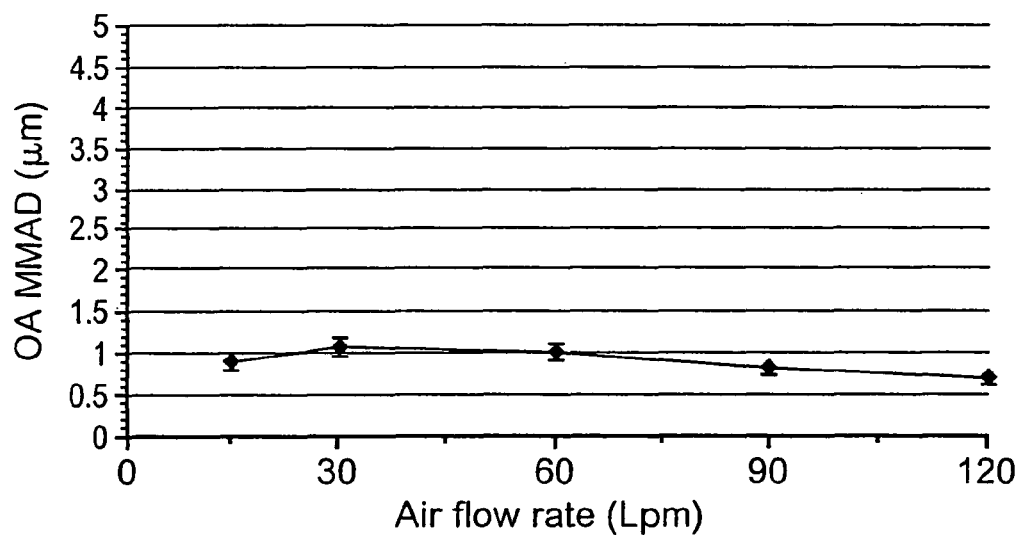
FIG. 26 shows the relationship between the MMAD of OA aerosol particles and air flow rate for a 5% w/w OA in PG solution.

FIG. 26 shows that at the standard MOUDI flow rate of 30 Lpm, the MMAD of OA aerosol particles is about 1.07 µm. Increasing the airflow rate to 90 and 120 Lpm, the MMAD of OA aerosol particles decreases by about 26% and 39%, respectively.

Figure 27:
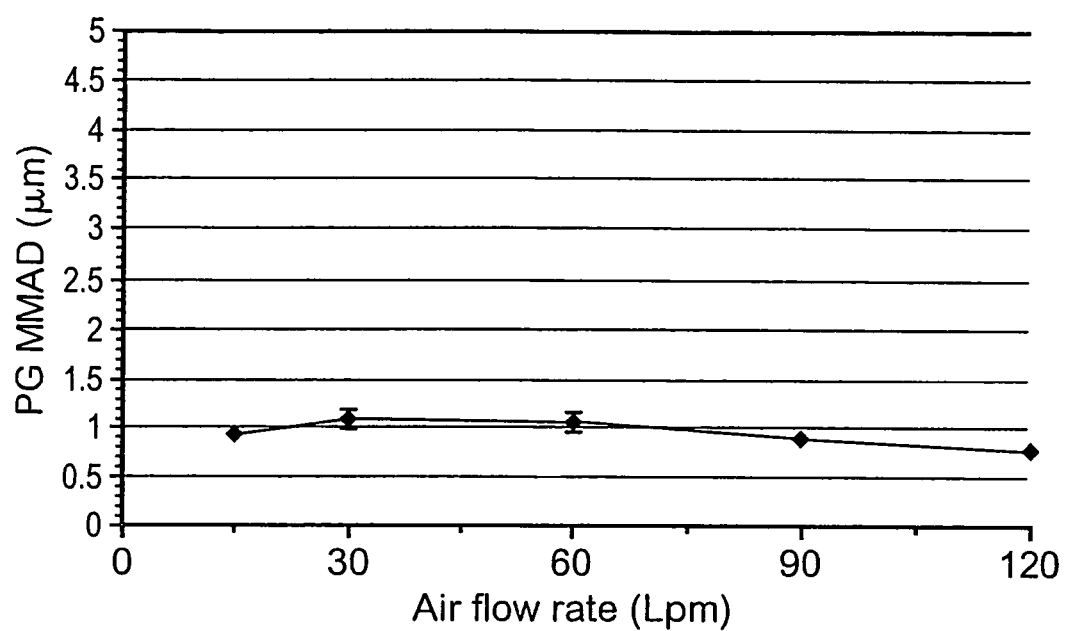
FIG. 27 shows the relationship between the MMAD of PG aerosol particles and air flow rate for a 5% w/w OA in PG solution.

FIG. 27 shows the MMAD of PG aerosol particles. Over the expected range of inhalation rates of the aerosol generator, 30 to 90 L/min, the particle size is relatively consistent.

The test results demonstrate that the length of the aerosol confinement sleeve can be selected to control aerosol particle size to enable the delivery of aerosols for different applications. For example, aerosols can be produced for delivering medicaments via inhalation for pulmonary delivery (utilizing small particle sizes) to upper respiratory tract delivery (utilizing larger particle sizes). Aerosols having a selected size distribution can be delivered over a broad range of inhalation rates. In addition, aerosol generating devices including an aerosol confinement sleeve can be used to produce aerosols having controlled aerosol size distributions for other applications, including the production of aerosols for forming coatings, such as paints, delivering scents, and depositing materials in microelectronic applications.

The above are exemplary modes of carrying out the invention and are not intended to be limiting. It will be apparent to those of ordinary skill in the art that modifications thereto can be made without departure from the spirit and scope of the invention as set forth in the accompanying claims.

What is claimed is:

1. A method for generating an aerosol, comprising:
   supplying liquid to a capillary sized flow passage having an outlet;
   heating the capillary sized flow passage so as to volatilize at least some of the liquid in the capillary sized flow passage; and
   directing the volatilized liquid into a confined air space enclosed within an aerosol confinement sleeve having a volume of about 0.05 $in^3$ to about 0.4 $in^3$.

2. The method of claim 1, further comprising forming an aerosol by directing the volatilized liquid out from the confined air space, wherein the aerosol formed has an MMAD (mass median aerosol diameter) of 0.2 to 0.5 µm or 1 to 2 µm.

3. The method of claim 1, wherein the directing the volatilized liquid into a confined air space comprises directing the volatilized liquid into a hollow cylinder.

4. The method of claim 1, wherein the directing the volatilized liquid into a confined air space comprises directing the volatilized liquid directly from the capillary sized flow passage into the confined air space, wherein an outer region of a body surrounding the capillary sized flow passage is in contact with an inner region of the confined air space to form a contiguous flow passage.

5. The method of claim 1, wherein the capillary sized flow passage is the lumen of a capillary tube, the method further comprising thermally insulating the capillary sized flow passage with a cylindrical body of a thermally insulating material in a surrounding relationship to the capillary tube.

6. The method of claim 1, wherein the directing the volatilized liquid into a confined air space causes condensation of at least some of the volatilized liquid within the confined air space.

7. The method of claim 1, wherein during the directing the volatilized liquid into a confined air space, air is prevented from flowing into the confined air space except at an outlet of the confinement sleeve.

8. The method of claim 1, wherein the directing the volatilized liquid into a confined air space comprises directing the volatilized liquid into the aerosol confinement sleeve with a length from about ⅛ inch to about 2 inches, a largest transverse dimension from about ⅛ inch to about ½ inch, and/or a ratio of a largest transverse dimension to a length thereof of from about 1:1 to about 0.25:4.

9. The method of claim 1, wherein the supplying liquid step comprises supplying a medicament, wherein the medicament is at least one substance selected from the group consisting of analgesics, anginal preparations, anti-allergics, antibiotics, antihistamines, antitussives, bronchodilators, diuretics, anticholinergics, hormones, and anti-flammatory agents.

10. A method for generating an aerosol, comprising:
supplying liquid to a capillary sized flow passage circumferentially surrounded by an insulating cylinder body having an outlet;
heating the capillary sized flow passage liquid so as to volatilize at least some of the liquid in the capillary sized flow passage; and
directing the volatilized liquid out of the outlet of the capillary sized flow passage into an aerosol confinement sleeve having an inner diameter of about ⅛ inch to about ½ inch located at the outlet of the insulating cylinder body,
wherein the aerosol confinement sleeve is located in contact with the insulating cylinder body, and wherein the inner diameter of the aerosol confinement sleeve is the same as the outer diameter of the insulating cylinder body.

11. The method of claim 10, wherein the aerosol confinement sleeve is a small diameter tube.

12. The method of claim 10, wherein the directing the volatilized liquid out of the outlet of the capillary sized flow passage into an aerosol confinement sleeve comprises directing the volatilized liquid out of the outlet of the capillary sized flow passage into the aerosol confinement sleeve with a confined air space having a volume about 0.05 in$^3$ to about 0.4 in$^3$.

13. The method of claim 10, wherein the directing the volatilized liquid out of the outlet of the capillary sized flow passage into an aerosol confinement sleeve comprises directing the volatilized liquid out of the outlet of the capillary sized flow passage into the aerosol confinement sleeve with a length from about ⅛ inch to about 2 inches, a largest transverse dimension from about ⅛ inch to about ½ inch, and/or a ratio of a largest transverse dimension to a length thereof of from about 1:1 to about 0.25:4.

14. The method of claim 10, wherein the supplying liquid step comprises supplying a medicament, wherein the medicament is at least one substance selected from the group consisting of analgesics, anginal preparations, anti-allergics, antibiotics, antihistamines, antitussives, bronchodilators, diuretics, anticholinergics, hormones, and anti-flammatory agents.

15. A method for generating an aerosol, comprising:
supplying liquid to a capillary sized flow passage;
heating the capillary sized flow passage so as to volatilize at least some of the liquid in the capillary sized flow passage; and
directing the volatilized liquid into a confined air space enclosed within an aerosol confinement sleeve,
wherein during the directing the volatilized liquid into the confined air space, air is prevented from flowing into the confined air space except at an outlet of the confinement sleeve.

16. The method of claim 15, wherein the directing the volatilized liquid into a confined air space comprises directing the volatilized liquid directly from the capillary sized flow passage into the aerosol confinement sleeve.

17. The method of claim 15, wherein the aerosol confinement sleeve comprises a hollow cylinder, and wherein the supplying liquid step comprises supplying a medicament, wherein the medicament is at least one substance selected from the group consisting of analgesics, anginal preparations, anti-allergics, antibiotics, antihistamines, antitussives, bronchodilators, diuretics, anticholinergics, hormones, and anti-flammatory agents.

18. A method for generating an aerosol, comprising:
supplying liquid to a capillary sized flow passage;
heating the capillary sized flow passage so as to volatilize at least some of the liquid in the capillary sized flow passage; and
directing the volatilized liquid into a confined air space enclosed within an aerosol confinement sleeve, wherein the confined air space has a volume of about 0.05 in$^3$ to about 0.4 in$^3$,
wherein during the directing the volatilized liquid into the confined air space, air is prevented from flowing into the confined air space except at an outlet of the confinement sleeve.

* * * * *